US012161738B2

(12) United States Patent
Cetti et al.

(10) Patent No.: US 12,161,738 B2
(45) Date of Patent: Dec. 10, 2024

(54) DEODORANT COMPOSITIONS

(71) Applicant: The Procter & Gamble Company, Cincinnati, OH (US)

(72) Inventors: Jonathan Robert Cetti, Mason, OH (US); David Frederick Swaile, Cincinnati, OH (US); Stevan David Jones, Hyde Park, OH (US); David Arthur Sturgis, Montgomery, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 140 days.

(21) Appl. No.: 16/835,351

(22) Filed: Mar. 31, 2020

(65) Prior Publication Data

US 2020/0306154 A1 Oct. 1, 2020

Related U.S. Application Data

(60) Provisional application No. 62/827,445, filed on Apr. 1, 2019.

(51) Int. Cl.
| | | |
|---|---|---|
| *A61K 8/19* | (2006.01) | |
| *A61K 8/02* | (2006.01) | |
| *A61K 8/04* | (2006.01) | |
| *A61K 8/34* | (2006.01) | |
| *A61Q 15/00* | (2006.01) | |

(52) U.S. Cl.
CPC .............. *A61K 8/19* (2013.01); *A61K 8/0229* (2013.01); *A61K 8/042* (2013.01); *A61K 8/046* (2013.01); *A61K 8/34* (2013.01); *A61Q 15/00* (2013.01); *A61K 2800/30* (2013.01); *A61K 2800/412* (2013.01); *A61K 2800/51* (2013.01); *A61K 2800/77* (2013.01)

(58) Field of Classification Search
CPC ........ A61K 8/19; A61K 8/0229; A61K 8/042; A61K 8/046; A61K 8/34; A61K 2800/30; A61K 2800/412; A61K 2800/51; A61K 2800/77; A61Q 15/00
See application file for complete search history.

(56) References Cited

U.S. PATENT DOCUMENTS

| | | | |
|---|---|---|---|
| 4,659,560 A | 4/1987 | Bews et al. | |
| 5,378,468 A | 1/1995 | Suffis et al. | |
| 5,512,274 A * | 4/1996 | Phinney | A61Q 15/00 424/65 |
| 9,314,412 B2 | 4/2016 | Phinney et al. | |

(Continued)

FOREIGN PATENT DOCUMENTS

| | | | | |
|---|---|---|---|---|
| AU | 8065498 A | * | 4/1999 | ............. A61Q 15/00 |
| BR | PI1004177 A2 | | 2/2013 | |

(Continued)

OTHER PUBLICATIONS

Dictionary.com, Humectant, 2020, screenshot of https://www.dictionary.com/browse/humectant?s=t (Year: 2020).*

(Continued)

*Primary Examiner* — Bethany P Barham
*Assistant Examiner* — Ayaan A Alam
(74) *Attorney, Agent, or Firm* — Alexandra S. Anoff

(57) ABSTRACT

A deodorant composition comprising a magnesium salt and an aqueous carrier, wherein the deodorant composition is substantially free of aluminum.

19 Claims, 3 Drawing Sheets

(56) References Cited

U.S. PATENT DOCUMENTS

| | | | |
|---|---|---|---|
| 9,468,596 | B2 | 10/2016 | Eizen |
| 10,413,490 | B2 | 9/2019 | Abuelhaiga |
| 10,543,164 | B2 | 1/2020 | Sturgis |
| 10,555,884 | B2 | 2/2020 | Sturgis |
| 2008/0213322 | A1* | 9/2008 | Birman ............... C09C 3/12 424/401 |
| 2012/0003284 | A1 | 1/2012 | Arnaud |
| 2014/0271517 | A1* | 9/2014 | Phinney ............... A61K 8/345 424/67 |
| 2016/0310498 | A1* | 10/2016 | Renucci ............... A61K 8/4926 |
| 2019/0000730 | A1* | 1/2019 | Abuelhaiga ............... C01F 5/14 |
| 2019/0000734 | A1 | 1/2019 | Sturgis |
| 2019/0298625 | A1 | 10/2019 | Hilliard, Jr. et al. |
| 2020/0000694 | A9 | 1/2020 | Sturgis |
| 2020/0368120 | A1* | 11/2020 | Ma ............... A61Q 1/02 |

FOREIGN PATENT DOCUMENTS

| | | |
|---|---|---|
| BR | 102012019695 A2 | 5/2014 |
| CN | 104688561 A | 6/2015 |
| EP | 0714655 A1 | 6/1996 |

OTHER PUBLICATIONS

Abrutyn, E., Deciphering chelating agent formulas, 2013, Cosmetics & toiletries, from https://www.cosmeticsandtoiletries.com/formulating/function/aids/premium-deciphering-chelating-agent-formulas-215885521.html (Year: 2013).*

Chemical Book, Magnesium Oxide, 2017, screenshot of https://www.chemicalbook.com/ChemicalProductProperty_EN_cb8853024.htm (Year: 2017).*

Database GNPD [Online] MINTEL; Sep. 27, 2006 (Sep. 27, 2006), anonymous: "Antiodorant Cream", XP055700751,retrieved from www.gnpd.com Database accession No. 590982.

Database GNPD [Online] MINTEL; Nov. 22, 2006 (Nov. 22, 2006) anonymous: "Fragrance Free Aluminium Free Deodorant", XP055700754,retrieved from www.gnpd.com, Database accession No. 621053.

Database GNPD [Online] MINTEL; Jan. 5, 2010 (Jan. 5, 2010), anonymous: "Everyday Deodorant",XP055700756, retrieved from www.gnpd.com, Database accession No. 1243385.

Database GNPD [Online] MINTEL; Jan. 24, 2011 (Jan. 24, 2011), anonymous: "Male Deodorising Wipes", XP055700758, retrieved from www.gnpd.com, Database accession No. 1473721.

Database GNPD [Online] MINTEL; Mar. 8, 2016 (Mar. 8, 2016), anonymous: "24h Deodorant Roll-On" XP055700761,retrieved from www.gnpd.com, Database accession No. 3850511.

Database GNPD [Online] MINTEL; Jan. 25, 2018 (Jan. 25, 2018), anonymous: "The Takesumi Detox Charcoal Underarm Detox Kit", XP055700767, retrieved from www.gnpd.com Database accession No. 5372805.

Database GNPD [Online] MINTEL;Jul. 27, 2018 (Jul. 27, 2018), anonymous: "Deodorant Roll-On", XP055700782, retrieved from www.gnpd.com, Database accession No. 5852019.

International Search Report and Written Opinion; Application Ser. No. PCT/US2020/025867; dated Jun. 15, 2020, 19 pages.

* cited by examiner

DEODORANT COMPOSITIONS

FIELD OF THE INVENTION

The present disclosure relates to deodorant compositions and methods relating thereto.

BACKGROUND OF THE INVENTION

Many consumers are seeking more natural, aluminum-free deodorant offerings, often mostly free of silicones. Often, these products will require a fragrance at a high enough level that it smells pleasant at application and throughout the day. They are further seeking products with lower irritation than they have experienced with baking soda based products. A challenge with formulating with fragrances is that they can be less stable in the presence of heat and extreme pH (either high or low). And products formulated with baking soda, which has a relatively high pH and high water solubility, can increase irritation. Highly water soluble alkaline powders contribute negatively towards fragrance oil stability as well, especially in a hot process needed to melt waxes.

Ingredients such as baking soda are typically put in anhydrous deodorant formulations, where the particle is dispersed in product formulations substantially free of water. The highly water-soluble alkaline powders contribute to effective malodor control when sweat dissolves the powder, but this can lead to irritation under the arm. High water solubility powders can also lead to gritty products, as the water-soluble powders can agglomerate when exposed to moisture released from powders during the hot batch process.

Aqueous deodorants are known in the art and can contain active ingredients. They have benefits of smoother feel at application, less residue, and ease of wash off. Aqueous deodorants, however, can often have a cold feel at application due to the evaporation of water. The key to maintaining adequate malodor control in these systems is having a product that maintains a hostile pH for bacteria. Actives that have a high-water solubility can raise the pH of the underarm above neutral for a short period of time, but the skin will quickly return to a neutral pH, where odor causing bacteria growth is favored, thus leading to body odor. Furthermore, highly water-soluble active ingredients such as baking soda can lead to increased fragrance and product instability due to some of the issues mentioned above. Particles that are not fully water soluble can give a poor product feel due to particle size being too large under the arm. Particles can furthermore settle in batch formulation if the structure of the system cannot suspend said particles.

Thus, there is a continuing challenge to formulate an aqueous or glycol containing non-aluminum, fragrance deodorant with acceptable product feel that provides low irritation while maintaining sufficient pH control throughout the day for odor protection.

SUMMARY OF THE INVENTION

A deodorant composition comprising a magnesium salt and an aqueous carrier, wherein the deodorant composition is substantially free of aluminum.

DETAILED DESCRIPTION OF THE INVENTION

Figure 1:
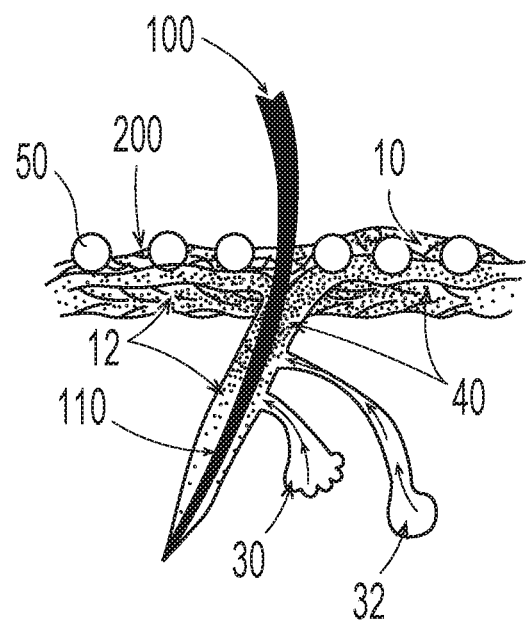
FIG. 1 is an illustration of a hair and hair follicle along with larger antimicrobial particles.

While the specification concludes with claims that particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

The components and/or steps, including those which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

The term "ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

The term "majority" refers to greater than about 51% of the stated component or parameter.

"Substantially free of" refers to about 2% or less, about 1% or less, or about 0.1% or less of a stated ingredient. "Free of" refers to no detectable amount of the stated ingredient or thing.

The term "volatile" as used herein refers to those materials that have a measurable vapor pressure at 25° C. Such vapor pressures typically range from about 0.01 millimeters of Mercury (mm Hg) to about 6 mmHg, more typically from about 0.02 mmHg to about 1.5 mmHg; and have an average boiling point at one (1) atmosphere of pressure of less than about 250° C., more typically less than about 235° C. Conversely, the term "non-volatile" refers to those materials that are not "volatile" as defined herein.

Water Solubility

The present inventors have discovered that the water solubilities of certain components in the deodorant have great importance. Materials having too high a solubility in aqueous formulations can have good ability to reduce odor initially, but they can lead to increased irritation and not be able to deliver sustained malodor control throughout the day because they are rapidly released after application. Materials having essentially no water solubility can be limited in terms of being soluble enough to inhibit bacteria growth. As such, materials having a low degree of solubility are preferred to give long lasting odor protection and bacterial control.

Materials with a high water solubility, such as a water solubility above 90 g/L @25° C., include but are not limited to: magnesium chloride, potassium carbonate, potassium bicarbonate, sodium carbonate, sodium sesquicarbonate, triethyl citrate, and baking soda. Materials with a low water solubility, such as a water solubility below 90 g/L @25° C., include but are not limited to: beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salicylic acid, phenoxyethanol, eugenol, linolenic acid, dimethyl succinate, citral, and triethyl citrate. Each of beryllium carbonate, magnesium carbonate, calcium carbonate, magnesium hydroxide, magnesium hydroxide and magnesium carbonate hydroxide, partially carbonated magnesium hydroxide, piroctone olamine, hexamidine, zinc carbonate, thymol, polyvinyl formate, salicylic acid, phenoxyethanol, eugenol, linolenic acid, dimethyl succinate, and citral have a water solubility below 75 g/L @25° C., below 50 g/L @25° C., below 1 g/L @25° C., and below 0.2 g/L @25° C.

Magnesium Salts

The present invention may comprise magnesium salts as an antimicrobial, for pH control or as a product feel aid. Magnesium salts may include, but are not limited to, magnesium hydroxide, magnesium carbonate, magnesium chloride, magnesium acetate, magnesium pidolate, magnesium gluconate, magnesium glutamate, magnesium heptagluconate, magnesium 2-ketogluconate, magnesium lactate, magnesium ascorbate, magnesium citrate, magnesium aspartate, magnesium pantothenate, magnesium bicarbonate, magnesium sorbate, magnesium nitrate, magnesium fulvate, magnesium sulfate, magnesium oxide, and combinations thereof. In one preferred aspect, the present invention may comprise magnesium chloride. In another preferred aspect, the present invention may comprise magnesium hydroxide. The present invention may comprise partially carbonated magnesium hydroxide as an antimicrobial. The deodorant compositions of the present invention may comprise from about 0.1% to about 30%, by weight of the deodorant, of one or more magnesium salts. In some embodiments, the deodorant composition may comprise from about 1% to about 20%, from about 2% to about 12%, from about 5% to about 20%, or from about 5% to about 10%, by weight of the deodorant, of one or more magnesium salts.

Magnesium hydroxide can provide good antimicrobial activity at high levels. Because it has a low water solubility (0.00064 g/100 ml at 25° C.) in aqueous or glycol formulations, the magnesium hydroxide particles can remain available for sweat to gradually dissolve them, and they can provide pH control throughout the day.

Partially carbonated magnesium hydroxide has a percentage of magnesium carbonate. Magnesium carbonate has a higher water solubility (0.0139 g/100 ml at 25° C.) thus increasing the pH control at earlier timepoints whilst maintain longer lasting pH control throughout the day. The partially carbonated magnesium hydroxide of the present invention may have from about 80% to about 100% in the form of magnesium hydroxide, by weight of the partially carbonated magnesium hydroxide, more preferably from about 85% to about 98%, or more preferably from about 80% to about 96% magnesium hydroxide, by weight of the partially carbonated magnesium hydroxide.

Figure 3:
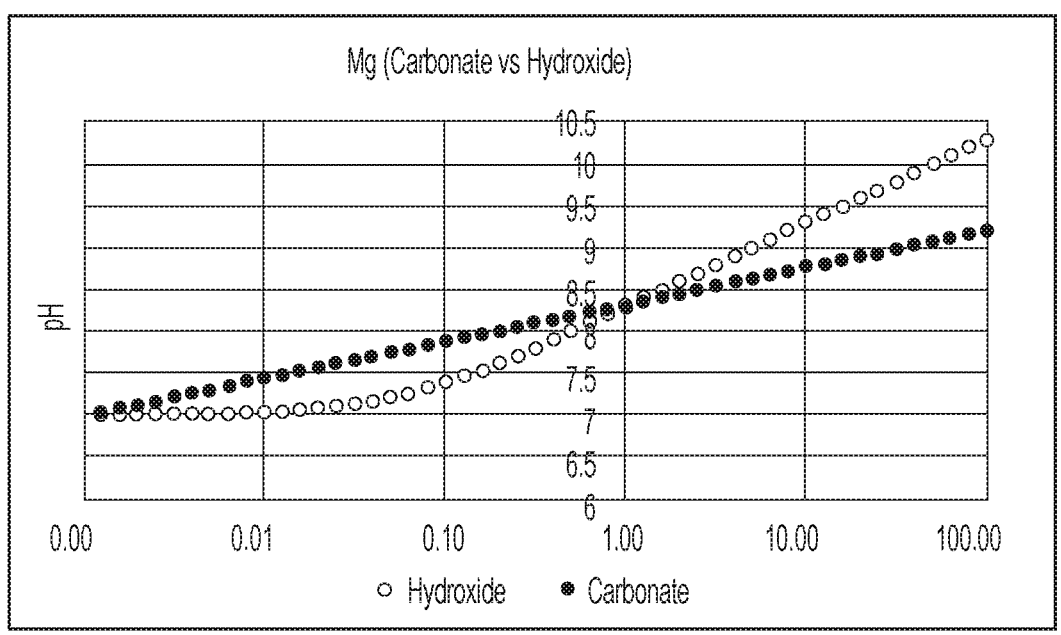
FIG. 3 is a mathematical model of data showing the solubility of magnesium carbonate and magnesium hydroxide.

FIG. 3 shows a mathematical model of data showing the log % solubility of magnesium carbonate and magnesium hydroxide. Magnesium hydroxide can increase the antimicrobial activity of aqueous deodorant formulations more effectively than magnesium carbonate, as magnesium hydroxide's pH ultimately rises higher. Magnesium hydroxide's lower solubility means it will remain longer and leave a reservoir available for maintaining a high pH throughout the day. That is, the low solubility of magnesium hydroxide means a delayed release so its benefit of providing a high pH is provided even after a while. Therefore, the combination of magnesium carbonate and magnesium hydroxide may be particularly effective over time.

Glycol

Aqueous deodorant formulations may optionally contain glycols. When used as a carrier, glycols are known to the art to promote a hostile environment for bacterial growth. Glycol materials may include but are not limited to dipropylene glycol, propylene glycol, 1,3 Propanediol, butylene glycol, tripropylene glycol, hexylene glycol, 1,2 hexane diol, PPG-10 butantediol, and polyethylene glycol.

Figure 4:
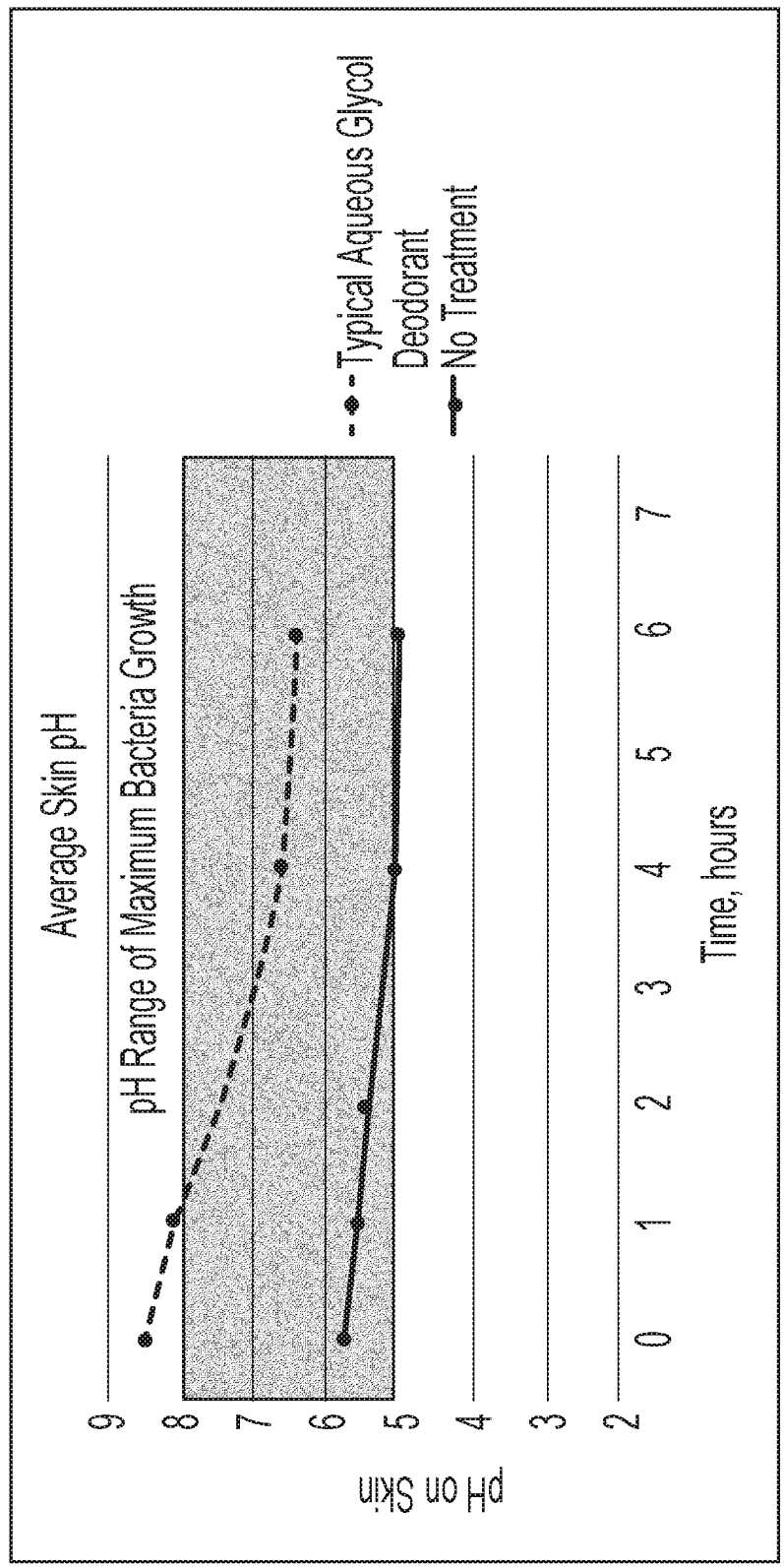
FIG. 4 is a graph of the change in pH under the arm throughout the day with an aqueous glycol formulation.

FIG. 4 is a graph of the change in pH under the arm throughout the day with an aqueous glycol formulation, and the change in pH under the arm throughout the day with no deodorant. As shown by the gray box in the figure, and as is known in the art, a pH between 5 and 8 provides optimal conditions for bacteria growth and subsequently underarm malodor. Therefore, it is beneficial for a deodorant to keep the pH of the underarm above at least 8. As shown in the graph, without any treatment, i.e., deodorant, the underarm pH mostly remains in the range of 5 to 8. The aqueous glycol formulation initially provides a high pH (above 8), but after 2 hours, the pH falls to a range of 5 to 8. This data shows that the aqueous glycol formulations, while able to provide initial protection against bacterial growth, are insufficient over time to maintain the higher pH needed to prevent bacterial growth. This highlights the need to add additional powders to maintain the higher pH for a longer duration of time.

Additional Antimicrobials

The present invention may include one or more antimicrobial compositions. For example, antimicrobials may include, without being limited to, piroctone olamine, hexamidine, magnesium carbonate, zinc carbonate, thymol, magnesium hydroxide, dead sea salt, magnesium hydroxide and magnesium carbonate hydroxide, calcium carbonate, polyvinyl formate, salycilic acid, niacinamide, phenoxyethanol, eugenol, linolenic acid, dimethyl succinate, citral, triethyl citrate, sepiwhite, baking soda, partially carbonated magnesium hydroxide, magnesium carbonate hydroxide, cinnamon essential oil, cinnamon bark essential oil, cinnamic aldehyde, and combinations thereof.

Table 1 below shows the raw material microbial inhibition concentration data tested against two key underarm bacteria strains. As can be seen, the first three listed antimicrobials, lupamin, hexamidine, and piroctone olamine, perform particularly well against the bacteria as raw materials. Also performing well as raw materials are phenoxyethanol, eugenol, linolenic acid, dimethyl succinate, citral, triethyl citrate, and sepiwhite. Also performing moderately well against the bacteria as raw materials were magnesium carbonate and magnesium hydroxide and calcium carbonate.

TABLE 1

| Antimicrobial | C. mucofaciens | S. epidermidis |
| --- | --- | --- |
| Lupamin | <2 ppm | 4 ppm |
| Hexamidine 36 mg/ml H2O | <2 ppm | 7 ppm |
| 100 mg/ml piroctone olamine in H2O | <5 ppm | 10 ppm |
| Polydialyldimethylammonium Chloride | 20 ppm | 10 ppm |
| 100% Phenoxyethanol | 400 ppm | 800 ppm % |
| Eugenol 99% ETOH | 773 ppm | 773 ppm |
| Linolenic Acid 70% ETOH | 1093 ppm | 1093 ppm |
| Dimethyl Succinate 98% ETOH | 1531 ppm | 3062 ppm |
| Citral 96% ETOH | 1500 ppm | 1500 ppm |
| 100% Triethyl citrate | 1600 ppm | 1600 ppm |
| Sepiwhite 40 mg/ml H2O ins | 2000 ppm | 1000 ppm |
| Magnesium Carbonate & Magnesium Hydroxide 50 mg/ml H2O ins | >2500 ppm | >2500 ppm |
| Ca Carbonate 50 mg/ml H2O ins | >2500 ppm | >2500 ppm |
| Linoleic acid 100% ETOH | 3125 ppm | 3125 ppm |
| Conarom B (beta Bio) 100% ETOH | 3125 ppm | 3125 ppm |
| Hexyl Decanol 97% ETOH | 6062 ppm | 3031 ppm |
| Ajowan oil 50% ETOH | 12500 ppm | 6300 ppm |
| Oregano oil 50% ETOH | 12500 ppm | 6300 ppm |
| 100% Ethylhexyl glycerin | 12500 ppm | 12500 ppm |
| Mineral oil 50% in ETOH | 12500 ppm | >50000 ppm |
| ACH 50% in H2O | 25000 ppm | 25000 ppm |
| NaCl 250 mg/ml H2O | >25000 ppm | >25000 ppm |
| Farnesol 95% ETOH | 47500 ppm | 5937 ppm |
| Phytol 97% ETOH | >49000 ppm | >49000 ppm |
| Nerolidol 98% ETOH | >49000 ppm | >49000 ppm |
| CaCl 500 mg/ml H2O | >50000 ppm | >50000 ppm |
| Isopropyl Myristate 98% ETOH | >59000 ppm | >59000 ppm |

While numerous antimicrobials exhibit efficacy against two main bacteria strains that deodorants try to address, due to regulatory and safety reasons, there are sometimes limits as to how much of a particular antimicrobial may be put into a deodorant formula. Therefore, there is a need for multiple antimicrobials to work together in a formula to deliver enough long-term odor protection.

Dipropylene glycol is known to the art to promote a hostile environment to bacterial growth. The inventors of the present invention believe that dipropylene glycol is an ideal carrier to combine with other antimicrobials. Deodorant compositions may comprise from about 0% to about 65%, from about 0% to about 50%, from about 10% to about 55%, from about 10% to about 50%, from about 20% to about 50%, from about 30% to about 50%, or from about 30% to about 55%, of any glycol disclosed herein, but dipropylene glycol in particular, by weight of the composition.

Additionally, the inventors of the present invention believe that piroctone olamine is an ideal antimicrobial to combine with other antimicrobials. Additionally, the inventors of the present invention believe that polydialyldimethylammonium chloride is an ideal antimicrobial to combine with other antimicrobials.

Polyquaternium may be present in the anhydrous cosmetic composition ranging from about 0.5% to about 20% by weight, or from about 1.0% to about 10% by weight, or from about 2% to about 8% by weight with respect to the total weight of the composition.

In general, the total amount of antimicrobial used in the present invention may be from about 0.1% to about 30%, by weight, of the deodorant. Some antimicrobials may be used in amounts as low as about 0.1%, by weight of the deodorant, such as if using piroctone olamine or hexamidine as the primary antimicrobial, while others could be as high as about 25%, such as if using magnesium hydroxide or magnesium hydroxide and magnesium carbonate hydroxide as the primary antimicrobial (primary antimicrobial being the antimicrobial present in the composition in the highest amount). In the latter cases, baking soda might still be used at a lower level, such as from about 0.1% to about 6%, as a secondary antimicrobial, or not at all.

Any of the antimicrobials of the present invention may be used as powders. It is believed that antimicrobial powders may provide a better deposition and have more longevity on the skin than antimicrobials delivered in a different form. While some powders may have a particle size from about 1 micron to about 100 microns, from about 1 micron to about 30 microns, or from about 1 micron to about 10 microns, it is believed that antimicrobial powders of a certain average particle size, typically from about 1 micron to about 5 microns, may provide a significant increase in antimicrobial efficacy.

Many antimicrobials can be effective at minimizing the skin surface bacteria. However, as a leave-on product where odor may not occur until later, even hours after application, antiperspirant and deodorant antimicrobials are needed that will be effective for long periods of time. So while antiperspirant and deodorant antimicrobials may be effective immediately upon application on the skin, it is believed that odor comes back quickly because the bacteria living around the hair follicle can quickly repopulate the skin surface bacteria. Historical approaches using high skin penetrating liquid antimicrobials to affect this region (for example, hexanediol) can cause irritation. Therefore, the present invention is able to target methods and mechanisms that can more effectively deliver antimicrobials not only to the skin surface, but to the bacteria in and around the hair follicle. While not wanting to be bound to the theory, the inventors of the present invention believe that powders, specifically powders with an average particle size of less than about 10 microns, in some cases from about 1 micron to about 5 microns, are more efficient at getting into the hair follicle where the bacteria live and repopulate the skin surface.

Figure 2:
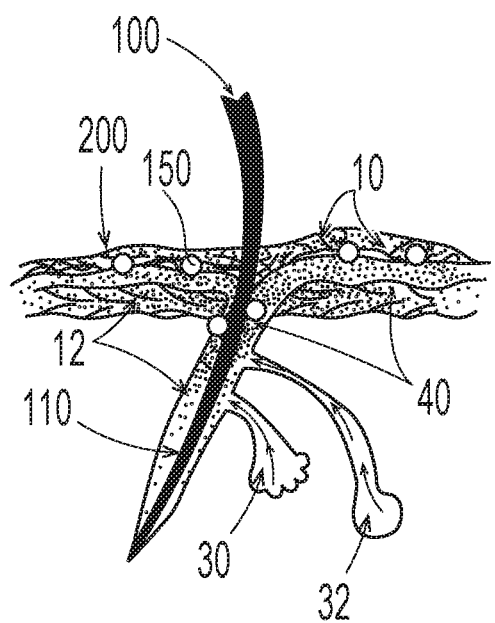
FIG. 2 is an illustration of a hair and hair follicle along with smaller antimicrobial particles.

As shown in FIGS. 1 and 2, a hair 100 is partly above the skin surface and partly below the skin surface in the hair follicle 110. The antimicrobial particles, 50 and 150, upon application, may be on the surface of the skin at the skin secretion/air/sweat interface 20 and where there is bacteria 10. As shown in FIGS. 1 and 2, the sebaceous gland 30 and the apocrine gland 32 in the skin have secretions that are in the hair follicle 110. Bacteria 12 and odor precursors 40 are embedded in the secretions. In FIG. 1, the larger antimicrobial particles 50 are too big to fit into the hair follicle, leaving the secretions inside the hair follicle untouched. The antimicrobial particles 50 come in contact with bacteria only on the surface of the skin. In FIG. 2, however, the antimicrobial particles 50 are sized to fit within the hair follicle and deliver antimicrobial activity not only to the surface of the skin, but also directly and immediately to the hair follicle secretions 12 and 40. Having the antimicrobial particles be in the range of about 1 to about 10 microns, in some embodiments about 1 to about 5 microns, provides better odor protection later in the day hours after application of the antiperspirant or deodorant when other good antimicrobial materials and other sizes of antimicrobial materials are not as effective against this rebound in bacteria population from the follicle.

Antiperspirant Compositions

Antiperspirant compositions can be formulated in many forms. For example, an antiperspirant composition can be, without limitation, a roll-on product, a body spray, a stick including soft solid sticks and invisible solids, or an aerosol. Each form can include the perfume materials to create an antiperspirant composition that can resist or eliminate habituation to the provided scent. Each of the antiperspirant compositions described below can include perfume materials as described herein.

A. Roll-On and Clear Gel

A roll-on antiperspirant composition can comprise, for example, water, emollient, solubilizer, deodorant actives, antioxidants, preservatives, or combinations thereof. A clear gel antiperspirant composition can comprise, for example, water, emollient, solubilizer, deodorant actives, antioxidants, preservatives, ethanol, or combinations thereof.

Water

The roll-on composition can include water. Water can be present in an amount of about 1% to about 99.5%, about 1% to about 30%, about 1% to about 50%, about 10% to about 30%, about 25% to about 99.5%, about 50% to about 95%, about 50% to about 99.5%, about 75% to about 99.5% about 80% to about 99.5%, from about 15% to about 45%, or any combination of the end points and points encompassed within the ranges, by weight of the deodorant composition.

Emollients

Roll-on compositions can comprise an emollient system including at least one emollient, but it could also be a combination of emollients. Suitable emollients are often liquid under ambient conditions. Depending on the type of product form desired, concentrations of the emollient(s) in the deodorant compositions can range from about 1% to about 95%, from about 5% to about 95%, from about 15% to about 75%, from about 1% to about 10%, from about 15% to about 45%, or from about 1% to about 30%, by weight of the deodorant composition.

Emollients suitable for use in the roll-on compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, C2 to C20 monohydric alcohols, C2 to C40 dihydric or polyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Deodorant Actives

Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the optional deodorant active may range from about 0.001%, from about 0.01%, of from about 0.1%, by weight of the composition to about 20%, to about 10%, to about 5%, or to about 1%, by weight of the composition.

Odor Entrappers

The composition can include an odor entrapper. Suitable odor entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Buffering Agent

The composition can include a buffering agent which may be alkaline, acidic or neutral. The buffer can be used in the composition for maintaining the desired pH. The composition may have a pH from about 7 to about 12, from about 7.5 to about 11.5, or from about 8 to about 11.

Suitable buffering agents include, for example, hydrochloric acid, sodium hydroxide, potassium hydroxide, and combinations thereof.

The compositions can contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

The deodorant compositions of the present invention may have a pH of at least about 8. In some embodiments, the deodorant may have a pH of at least about 9 or at least about 10. And after application to the underarm, the pH of the underarm 6 hours later may still be at least about 8, as shown below in the data in Table 6.

Chelator

The deodorant compositions may comprise a chelator. Specific and/or additional chelators in the present invention may include, but are not limited to, diethylenetriaminepentaacetic acid (DTPA), diethylenetriaminepentakis (methylenephosphonic acid) (DTPMP), desferrioxamine, their salts and combinations thereof, EDTA, DPTA, EDDS, enterobactin, desferrioxamine, HBED, and combinations thereof. The amount of chelant, by weight of composition, may be from about 0.05% to about 4%.

Solubilizer

The composition can contain a solubilizer. A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof.

Suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenated castor oil.

When the solubilizing agent is present, it is typically present at a level of from about 0.01% to about 5%, alternatively from about 0.01% to about 3%, alternatively from about 0.05% to about 1%, alternatively from about 0.01% to about 0.05%, by weight of the composition.

Preservatives

The composition can include a preservative. The preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name German® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

B. Body Spray

A body spray can contain, for example, a carrier, perfume, a deodorant active, odor entrappers, propellant, or combinations thereof. The body spray compositions can be applied as a liquid.

Carrier

A carrier suitable for use in a body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. A suitable example of an alcohol can include ethanol.

Propellant

The compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2, 2-tetrafluoroethane (propellant 114), 1-chloro-1,1-difluoro-2,2-trifluoroethane (propellant 115), 1-chloro-1,1-difluoro-ethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 difluoroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42%, or any combination thereof, by weight of the total fill of materials stored within the container.

C. Soft Solid

Soft solid composition can comprise volatile silicone, antiperspirant active, gellant, residue masking material, or combinations thereof. In addition, soft solids generally have a hardness value after dispensing of about 500 gram force or less.

Volatile Silicone Solvent

The soft solid can comprises a volatile silicone solvent at concentrations ranging from about 20% to about 80%, preferably from about 30% to about 70%, more preferably from about 45% to about 70%, by weight of the composition. The volatile silicone of the solvent may be cyclic or linear.

"Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27-32 (1976), which descriptions are incorporated herein by reference. Preferred volatile silicone materials are those having from about 3 to about 7, preferably from about 4 to about 5, silicon atoms.

Cyclic volatile silicones are preferred for use in the antiperspirant compositions herein, and include those represented by the formula:

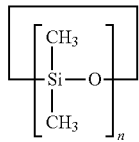

wherein n is from about 3 to about 7, preferably from about 4 to about 5, most preferably 5. These cyclic silicone materials will generally have viscosities of less than about 10 centistokes at 25° C.

Linear volatile silicone materials suitable for use in the antiperspirant compositions include those represented by the formula:

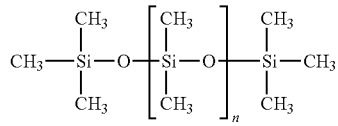

wherein n is from about 1 to about 7, preferably from about 2 to about 3. These linear silicone materials will generally have viscosities of less than about 5 centistokes at 25° C.

Specific examples of volatile silicone solvents suitable for use in the antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Gellant Material

The soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent described hereinbefore, provides the composition with a physically stable structure within which the particulate antiperspirant materials are dispersed, and maintained as such over an extended period of time.

Specifically, the gellant material can comprise saturated or unsaturated, substituted or unsubstituted, fatty alcohols or mixtures of fatty alcohols having from about 20 to about 60 carbons atoms, preferably from about 20 to about 40 carbon atoms. Preferred are combinations of the fatty alcohols. The fatty alcohol gellants are preferably saturated, unsubstituted monohydric alcohols or combinations thereof, which have a melting point of at less than about 110° C., more preferably from about 60° to about 110° C., even more preferably between about 100° C. and 110° C.

It has been found that this fatty alcohol-based gellant material, when combined with volatile silicone solvents provides a stable structure for maintaining a dispersion of particulate antiperspirant material in a topical formulation without the necessity of using conventional particulate thickening agents. This gellant material is especially useful in maintaining the physical stability of particulate dispersions containing higher concentrations of volatile silicone solvents.

It was also found that penetration force values for the antiperspirant compositions can be controlled by adjusting total fatty alcohol concentrations. In controlling penetration force values in this manner, there is no longer a need to use organic solvents or thickening agents to control penetration force values, which solvents or thickening agents often add cost to the formulation, introduce additional compatibility issues, and often contribute undesirable cosmetics such as prolonged stickiness, difficulty in ease of spreading, increased dry-down times and reduced dry feel after application.

Specific concentrations of the gellant materials can be selected according to the desired penetration force value. For roll-on formulations having a penetration force value of from about 20 gram·force to about 100 gram·force, gellant material concentrations preferably range from about 0.1% to about 3%, preferably from about 1.5% to about 3%, by weight of the antiperspirant composition. For other cream formulations, including those formulations suitable for use in cream applicator devices, which have a penetration force value of from about 100 gram·force to about 500 gram·force, gellant material concentrations preferably range from about 3% to about 8%, preferably from about 3% to about 6%, by weight of the antiperspirant composition.

Specific examples of fatty alcohol gellants for use in the antiperspirant compositions that are commercially available include, but are not limited to, Unilin® 425, Unilin® 350, Unilin®550 and Unilin® 700 (supplied by Petrolite)

Residue Masking Material

The soft solid compositions can further comprise a nonvolatile emollient as a residue masking material. Such materials and their use in antiperspirant products are well known in the antiperspirant art, and any such material may be incorporated into the composition of the present invention, provided that such optional material is compatible with the essential elements of the composition, or does not unduly impair product performance or cosmetics.

Concentrations of the optional residue masking material can range from about 0.1% to about 40%, preferably from about 1% to about 10%, by weight of the antiperspirant composition. These optional materials can be liquid at ambient temperatures, and can be nonvolatile. The term "nonvolatile" as used in this context refers to materials which have a boiling point under atmospheric pressure of at least about 200° C. Nonlimiting examples of suitable residue masking materials for use in the antiperspirant products include butyl stearate, diisopropyl adipate, petrolatum, nonvolatile silicones, octyldodecanol, phenyl trimethicone, isopropyl myristate, C12-15 ethanol benzoates and PPG-14 Butyl Ether. Residue masking materials are described, for example, in U.S. Pat. No. 4,985,238, which description is incorporated herein by reference.

Other Materials

The soft solid compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance.

Non limiting examples of materials can include active components such as bacteriostats and fungiostats, and "nonactive" components such as colorants, perfumes, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

Examples—Gel Deodorant

The following aqueous glycol formulations in Table 2 were made by heating all of the ingredients to 85° C. and using typical mixing procedures known to those of ordinary skill in the art. All ingredients, excluding fragrance, are heated to 85° C. When all materials are homogeneous the formulation is held at 85° C. for a minimum of 10 minutes. The temperature is reduced to 74° C., at which point the fragrance is added. The formulation is poured into a canister suitable for a gel or stick underarm product and then allowed to cool.

balanced design with half of the panelists having Comparative Example 1 on the left and half with Comparative Example 1 on the right. Panelists evaluated the following questions at each of the timepoints:

Application & Initial Cosmetic Evaluations (After controlled dosage application of 0.6 g product per underarm with shirt off, the following questions were answered):

Amount of Product Glide ((0-10 pt scale with anchors of "Not at All" to "Extreme Amount)";

Dry Feel of Product (0-10 pt scale with anchors of "Not at All" to "Extreme Amount)";

Cold Feel (0-10 pt scale with anchors of "Not at All" to "Extreme Amount)";

Feeling Sticky (0-10 pt scale with anchors of "Not at All" to "Extreme Amount)";

Feeling Greasy (0-10 pt scale with anchors of "Not at All" to "Extreme Amount)".

Feeling Clean (0-10 pt scale with anchors of "Not at All" to "Extreme Amount).

The following data in Table 3 shows that Example 2, containing partially carbonated magnesium hydroxide, had significantly less cold feel at application compared to Comparative Example 1, not containing partially carbonated magnesium hydroxide.

TABLE 2

| CAS | Ingredient Tradename | Chemical Name | Comparative Example 1 Aqueous Glycol Deodorant Control % | Inventive Example 2 Aqueous Glycol Deodorant Containing Partially Carbonated Magnesium Hydroxide % |
|---|---|---|---|---|
| 7732-18-5 | Water | Water | 25.88 | 19.55 |
| 1309-42-8 39409-82-0 | CareMag D | Partially Carbonated Magnesium Hydroxide | — | 8.00 |
| 25265-71-8 | Dipropylene Glycol | Dipropylene Glycol Low Odor | 42.76 | 41.00 |
| 57-55-6 | Propylene Glycol USP/EP | Propylene Glycol | 17.88 | 18.00 |
| 26316-40-5 | Pluracare 1307 Prill | Pluracare 1307 Prill | 3.03 | 3.00 |
| 135326-54-4 | Tegosoft APM | PPG-3 Myristyl Ether | 1.75 | 1.75 |
| 124-68-5 | Aminomethyl Propanol 95% | Aminomethyl Propanol | 0.15 | 0.15 |
| 13235-36-4 | Versene 220 | Tetrasodium EDTA | 0.05 | 0.05 |
| 822-16-2 | Sodium Stearate OP-200V | Sodium Stearate | 5.50 | 5.50 |
| mixture | Fragrance | Fragrance | 3.00 | 3.00 |
| | | Total | 100 | 100 |

Aqueous deodorant formulations can feel cold at application, which can be a consumer negative. The addition of magnesium hydroxide however can make the product feel less cold at application.

A study to understand application effects of the addition of magnesium hydroxide was done comparing Comparative Example 1, not containing magnesium hydroxide, with Example 2, containing partially carbonated magnesium hydroxide. 36 male panelists were recruited. Products were blinded with 3 digit codes and randomized using a complete

TABLE 3

| Assessment at Application | Comparative Example 1 Aqueous Glycol Deodorant Control | Inventive Example 2 Aqueous Glycol Deodorant Containing Partially Carbonated Magnesium Hydroxide |
|---|---|---|
| Glide at Application | 6.06 | 5.61 |
| Dry Feel at Application | 3.31 | 3.69 |

TABLE 3-continued

|  | Comparative Example 1 Aqueous Glycol Deodorant Control Assessment at Application | Inventive Example 2 Aqueous Glycol Deodorant Containing Partially Carbonated Magnesium Hydroxide |
|---|---|---|
| Cold Feel at Application | 4.19 | 3.53[s] |
| Feeling Sticky Application | 5.14 | 4.78 |
| Feeling Greasy Application | 4.11 | 3.94 |
| Feeling Clean at Application | 5.22 | 5.31 |

[s]Significant at 90% confidence interval.

The inclusion of a magnesium salt such as magnesium hydroxide can lead to improved malodor control. When combined with another antimicrobial or glycol carrier, it can extend the formulation ability to maintain a hostile environment under the arm by maintaining a high pH beyond what can be done with a formulation without the inclusion of magnesium hydroxide. Even 6 hours after applying the inventive deodorant to the underarm, the pH of the underarm may remain above 8, which inhibits bacterial growth.

The inclusion of magnesium salts in aqueous glycol formulations can also lead to improved residue control compared to their inclusion in anhydrous sticks. Anhydrous products require high amounts of waxes and non-volatile compounds that lead to heavy residue under the arms and on the clothes. Aqueous and aqueous glycol formulations do not require these materials leading to less residue.

Test Methods

Tier 1 Anaerobic MIC Assay

The data in Table 1 above was generated with the following test method. The purpose of this assay is to determine if a compound or formulation has an antimicrobial effect in vitro.

It is understood that when not specifically noted in this procedure:

a) All materials, reagents and equipment required for this procedure are of appropriate design and condition of cleanliness and/or sterility as determined by their intended use.
b) The operator has been trained in aseptic technique and has been qualified to perform the procedure and accurately interpret the results.
c) All media required for this procedure was manufactured by a reputable commercial source egg. Difco, Merck etc. and has been stored and prepared as per manufacturer's instructions.
d) All routine laboratory controls, including but not limited to, media function and growth promotion tests, verification of sterility and use of positive and negative controls are being conducted.

Procedure: (All procedures performed in anaerobic chamber except where noted)

1. Apparatus

Incubator at 37° C.; 20-200 ul 12 channel pipette; 5-50 ul 12 channel pipette; 1250 ul 8 channel Thermo Scientific Matrix pipette; 96 well plate shaker (located in incubator); Beckman Coulter deep well cap mat #267005; Beckman Coulter deep well 96 well plates #267007; Falcon 96 well tissue culture plates #353072; Vortexer; Culture tubes/caps Disposable sterile gloves; Sterile petri dishes; Standard microbiological lab equipment (sterile pipettes, syringes, tips, loops, etc.); Glass bottles/flasks for media; Autoclave; Parafilm; Spectrophotometer.

2. Media 0.9% or 0.85% saline solution
BHI agar supplemented with 1% Tween 80
BHI media supplemented with 1% Tween 80

3. Microbial Strains

*Staphylococcus epidermidis* (clinical isolate)
*Corynebacterium mucofaciens* (clinical isolate)

4. Test Procedure

Inoculum Preparation

Prior to testing streak organisms for isolation on BHI with 1% Tween 80 plates, wrap with parafilm and place in 37° C. incubator. When isolated colonies appear remove one representative colony from each plate and place each in 5 ml of BHI with 1% Tween 80 media. Incubate at 37° C. with shaking overnight. Inoculate 20 ml BHI with 1% Tween 80 (per 96 deep well plate to be tested) with 20 ul of the overnight culture (1-1000 dilution).

Master Plate Preparation

Compounds/formulations to be tested are diluted across a 96 deep well plate as shown below (for a 1% stock solution). 800 ul of 0.85% saline is added to wells A1 and B1 (as these will be the negative and positive control respectively). 800 ul each 1% stock solution+positive control are added to wells C1 through H1. 400 ul 0.85% saline are added to all other wells. 400 ul is then removed from #1 well added to the #2 well and mixed. This is then continued across the plate resulting in a 50% dilution between wells across the plate (this can be easily accomplished with an automatic 8 channel Matrix pipette set to withdraw, dispense and mix).

|  | 1 | 2 | 3 | 4 | 5 | 6 |
|---|---|---|---|---|---|---|
| A | 800 ul saline | 400 ul NaCl | 400 ul NaCl | 400 ul NaCl | 400 ul NaCl | 400 ul NaCl |
| B | 800 ul saline | 400 ul NaCl | 400 ul NaCl | 400 ul NaCl | 400 ul NaCl | 400 ul NaCl |
| C | 800 ul + control | 400 ul NaCl | 400 ul NaCl | 400 ul NaCl | 400 ul NaCl | 400 ul NaCl |
| D | 800 ul compound 1 | 400 ul NaCl | 400 ul NaCl | 400 ul NaCl | 400 ul NaCl | 400 ul NaCl |
| E | 800 ul compound 2 | 400 ul NaCl | 400 ul NaCl | 400 ul NaCl | 400 ul NaCl | 400 ul NaCl |
| F | 800 ul compound 3 | 400 ul NaCl | 400 ul NaCl | 400 ul NaCl | 400 ul NaCl | 400 ul NaCl |
| G | 800 ul compound 4 | 400 ul NaCl | 400 ul NaCl | 400 ul NaCl | 400 ul NaCl | 400 ul NaCl |
| H | 800 ul compound 5 | 400 ul NaCl | 400 ul NaCl | 400 ul NaCl | 400 ul NaCl | 400 ul NaCl |

|  | 7 | 8 | 9 | 10 | 11 | 12 |
|---|---|---|---|---|---|---|
| A | 400 ul NaCl | 400 ul NaCl | 400 ul NaCl | 400 ul NaCl | 400 ul NaCl | 400 ul NaCl |
| B | 400 ul NaCl | 400 ul NaCl | 400 ul NaCl | 400 ul NaCl | 400 ul NaCl | 400 ul NaCl |
| C | 400 ul NaCl | 400 ul NaCl | 400 ul NaCl | 400 ul NaCl | 400 ul NaCl | 400 ul NaCl |
| D | 400 ul NaCl | 400 ul NaCl | 400 ul NaCl | 400 ul NaCl | 400 ul NaCl | 400 ul NaCl |
| E | 400 ul NaCl | 400 ul NaCl | 400 ul NaCl | 400 ul NaCl | 400 ul NaCl | 400 ul NaCl |
| F | 400 ul NaCl | 400 ul NaCl | 400 ul NaCl | 400 ul NaCl | 400 ul NaCl | 400 ul NaCl |

|   | 1 | 2 | 3 | 4 | 5 | 6 | 7 |
|---|---|---|---|---|---|---|---|
| G | 400 ul NaCl | 400 ul NaCl | 400 ul NaCl | 400 ul NaCl | 400 ul NaCl | 400 ul NaCl |   |
| H | 400 ul NaCl | 400 ul NaCl | 400 ul NaCl | 400 ul NaCl | 400 ul NaCl | 400 ul NaCl |   |

|   | 1 | 2 | 3 | 4 | 5 | 6 | 7 |
|---|---|---|---|---|---|---|---|
| A | Media Blank | Media Blank | Media Blank | Media Blank | Media Blank | Media Blank | Media Blank |
| B | Pos | Pos | Pos | Pos | Pos | Pos | Pos |
| C | 0.1 | 0.05 | 0.025 | 0.0125 | 0.00625 | 0.003125 | 0.0015625 |
| D | 0.1 | 0.05 | 0.025 | 0.0125 | 0.00625 | 0.003125 | 0.0015625 |
| E | 0.1 | 0.05 | 0.025 | 0.0125 | 0.00625 | 0.003125 | 0.0015625 |
| F | 0.1 | 0.05 | 0.025 | 0.0125 | 0.00625 | 0.003125 | 0.0015625 |
| G | 0.1 | 0.05 | 0.025 | 0.0125 | 0.00625 | 0.003125 | 0.0015625 |
| H | 0.1 | 0.05 | 0.025 | 0.0125 | 0.00625 | 0.003125 | 0.0015625 |

|   | 8 | 9 | 10 | 11 | 12 |
|---|---|---|----|----|----|
| A | Media Blank | Media Blank | Media Blank | Media Blank | Media Blank |
| B | Pos | Pos | Pos | Pos | Pos |
| C | 0.00078125 | 0.000390625 | 0.000195313 | 9.76563E−05 | 4.88281E−05 |
| D | 0.00078125 | 0.000390625 | 0.000195313 | 9.76563E−05 | 4.88281E−05 |
| E | 0.00078125 | 0.000390625 | 0.000195313 | 9.76563E−05 | 4.88281E−05 |
| F | 0.00078125 | 0.000390625 | 0.000195313 | 9.76563E−05 | 4.88281E−05 |
| G | 0.00078125 | 0.000390625 | 0.000195313 | 9.76563E−05 | 4.88281E−05 |
| H | 0.00078125 | 0.000390625 | 0.000195313 | 9.76563E−05 | 4.88281E−05 |

Test Plate Preparation

In row A of a 96 deep well plate pipette 180 ul of sterile BHI with 1% Tween 80 as a negative growth control. All other wells receive 180 ul of inoculum. From the master plate introduce 20 ul to the corresponding row in the test plate using an 8-channel pipette. Loaded plates are placed on a plate shaker in the 37° C. incubator and incubated overnight. The next day read the O.D. 600 on a plate reader. The MIC is the last well from the right that has no bacterial growth.

pH of Various Magnesium Salts

The pH of magnesium carbonate, partially carbonated magnesium hydroxide, magnesium hydroxide and magnesium oxide were taken in a water solution. The pH values were recorded as follows in Table 4. All magnesium salts show that the pH alkaline, between 9.6 and 10.8 depending on the magnesium salt selected. Magnesium oxide had the highest pH observed.

TABLE 4

|   | pH in water 12% Solution |
|---|---|
| Magnesium Carbonate | 9.6 |
| Partially Carbonated Magnesium Hydroxide | 9.6 |
| Magnesium Hydroxide | 10 |
| Magnesium Oxide | 10.8 |

Product Efficacy Test

The following formulations were tested in a product efficacy test.

TABLE 5

| INGREDIENT | Comparative Example 2 Aqueous Glycol Deodorant Control % | Inventive Example 3 Aqueous Glycol Deodorant Containing Partially Carbonated Magnesium Hydroxide % |
|---|---|---|
| Dipropylene Glycol | 45 | 52 |
| Water | 23 | 15.1 |
| Propylene Glycol | 18 | 11 |
| Partially Carbonated Magnesium Hydroxide | 0 | 8 |
| Sodium Stearate | 5 | 5.5 |
| Fragrance | 4 | 4 |
| Poloxamine 1307 | 3 | 3 |
| PPG-3 Myristyl Ether | 1.4 | 1.4 |
| Tetrasodium EDTA | 0.5 | 0 |
| Blue 1 | 0.0009 | 0 |
| Total | 100.00 | 100.00 |

The product efficacy test quantifies total biomass on the underarm by analysis of swabs placed in liquid media then analyzed with a Soleris system for rapid microbial detection. The method is most applicable to broad spectrum antimicrobial technologies and/or technologies where there is a correlation between activity against organism(s) of interest and total microbial biomass on the underarm.

The test begins with a washout phase (4 days) where 6 test subjects were asked to refrain from use of any underarm product. During this time, they were provided with a soap for washing. During the treatment phase, test subjects apply 0.6 g per underarm of the two products to be tested in a paired comparison manner.

Swabs are collected from underarms of each panelist prior to the first treatment (Day 1, time 0) and Day 3 (6 hours after application) and Day 4 (6 hours after application). The pH is measured under the arm prior to the first treatment (Day 1, time 0) and on Day 4 (6 hours after application) by holding the probe of a pH meter under the arm until the pH reading has stabilized. Swabs are analyzed for bacterial growth using a Soleris system for rapid microbial detection. The Soleris detects time for a predetermined bacterial count measured by growth in the liquid media. The longer the time to detect growth (higher bar on the chart) the lower the bacterial count.

The sampling method is described as follows:
1. Beginning with the right underarm, a Copan sterile swab is dipped in distilled water.
2. Identify the midline of the Subject's RIGHT armpit. Starting just left of the midline of the underarm (Site R1) of the Subject's RIGHT armpit, press the swab firmly against the skin and in a vertical direction run the swab up and down for 10 strokes traveling approximately 4 inches per stroke. One stroke is 1 upward motion and 1 downward motion. After each stroke, rotate the swab approximately one-half turn.
3. Once swabbing in Site R1 is complete, the swab will be returned to the labeled sterile transport tube and placed immediately on wet ice.
4. A second Copan swab will be removed from labeled transport tube and dipped in distilled water.
5. Identify the midline (Site R2) of the Subject's RIGHT armpit. Press the swab firmly against the skin and in a vertical direction run the swab up and down the skin for 10 strokes. 1 stroke is (one upward motion and 1 downward motion). After each stroke rotate the swab approximately one-half turn.
6. Once swabbing in Site R2 is complete, the swab will be returned to the labeled sterile transport tube and placed immediately on wet ice.
7. A third Copan swab will be removed from labeled transport tube and dipped in distilled water.
8. Identify the midline of the Subject's RIGHT armpit. Starting just right of the midline (Site R3) of the Subject's RIGHT armpit, press the swab firmly against the skin and in a vertical direction run the swab up and down the skin for 10 strokes. 1 stroke is (one upward motion and 1 downward motion). After each stroke rotate the swab approximately one-half turn.
9. Once swabbing in Site R3 is complete, the swab will be returned to the labeled sterile transport tube and placed immediately on wet ice.
10. Samples will be collected from the LEFT armpit.
11. The Copan sterile swab is dipped in distilled water.
12. Identify the midline of the Subject's LEFT armpit. Starting just right of the midline of the underarm (Site L4) of the Subject's LEFT armpit, press the swab firmly against the skin and in a vertical direction run the swab up and down for 10 strokes. One stroke is 1 upward motion and 1 downward motion. After each stroke, rotate the swab approximately one-half turn.
13. Once swabbing in Site L4 is complete, the swab will be placed in the designated swab tube and the tube will be placed immediately on wet ice.
14. A second Copan swab will be dipped in distilled water.
15. Identify the midline (Site L5) of the Subject's LEFT armpit. Press the swab firmly against the skin and in a vertical direction run the swab up and down the skin for 10 strokes. 1 stroke is (one upward motion and 1 downward motion). After each stroke rotate the swab approximately one-half turn.
16. Once swabbing in Site L5 is complete, the swab will be placed in the swab tube and the tube will be placed immediately on wet ice.
17. A third Copan swab will be dipped in distilled water.
18. Identify the midline of the Subject's LEFT armpit. Starting just left of the midline (Site L6) of the Subject's LEFT armpit, press the swab firmly against the skin and in a vertical direction run the swab up and down the skin for 10 strokes. 1 stroke is (one upward motion and 1 downward motion). After each stroke rotate the swab approximately one-half turn.
19. Once swabbing in Site L6 is complete, the swab will be placed in the swab tube and the tube will be placed immediately on wet ice.
20. Swabs are aseptically clipped into NF-TVC vials and placed in the Soleris instrument where they are incubated at 34° C., detection threshold 12, skip factor 1 and a shut eye of 20.

TABLE 6

Underarm pH readings

| | Comparative Example 2 Aqueous Glycol Deodorant Control | Inventive Example 3 Aqueous Glycol Deodorant Containing Partially Carbonated Magnesium Hydroxide |
|---|---|---|
| pH of product | 9.5 | 10.2 |
| Initial underarm pH (Baseline, Day 1) | 6.0 | 6.1 |
| Day 4 pH After Application (6 hours after application #4) | 7.3 | 9.0 |

The underarm pH readings show that the pH of the inventive formula, Example 3, is raised more than the Comparative Example 2. In addition, Example 3 maintains the pH under the arm above 8, even 6 hours later, thus providing a more hostile environment compared to the pH of 7.3 under the arm for Example 2.

Table 7 below shows average detection time for the swabs. The longer the detection time indicates less bacteria was present in the test subjects underarm. The data below represents the average detection time for six test subjects.

TABLE 7

| | Comparative Example 2 Aqueous Glycol Deodorant Control | Example 3 Aqueous Glycol Deodorant Containing Partially Carbonated Magnesium Hydroxide |
|---|---|---|
| Initial Detection Time (Baseline, Day 1) | 8.55 | 8.35 |
| Day 3 Detection Time (6 hours after application) | 11.33 | 12.17 |
| Day 4 Detection Time (6 hours after application) | 11.83 | 14.03 |

This data in Table 7 shows that the Inventive formula, Example 3, is better at preventing bacterial growth, i.e., it takes longer for a set amount of bacteria to grow, than the comparative formula. This is an indication of the effectiveness of an aqueous formulation comprising a glycol and partially carbonated magnesium hydroxide.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

What is claimed is:

1. A deodorant composition comprising:
   a. from about 5% to about 20%, by weight of the composition, of a partially carbonated magnesium hydroxide having a water solubility below 90 g/L at 25° C. and a pH of at least 9.6 in water 12% solution;
   b. from about 10% to about 55%, by weight of the composition, of dipropylene glycol;
   c. a buffering agent comprising sodium hydroxide; and
   d. a perfume;
   wherein the deodorant composition is substantially free of aluminum; and
   wherein the composition has a pH of at least about 8.

2. The deodorant composition according to claim 1, wherein the partially carbonated magnesium hydroxide comprises magnesium carbonate and from about 85% to about 98%, by weight of the partially carbonated magnesium hydroxide, magnesium hydroxide.

3. The deodorant composition according to claim 1, wherein the partially carbonated magnesium hydroxide comprises magnesium carbonate and from about 80% to about 96%, by weight of the partially carbonated magnesium hydroxide, magnesium hydroxide.

4. The deodorant composition of claim 1, wherein the composition further comprises from about 50% to about 95%, by weight of the composition, water.

5. The deodorant composition of claim 1, wherein the composition comprises from about 30% to about 65% of dipropylene glycol, by weight of the composition.

6. The deodorant composition of claim 1, wherein 6 hours after application of the deodorant composition to an underarm, the underarm pH is at least 8.

7. The deodorant composition of claim 1, wherein the composition is a gel and/or a spray.

8. The deodorant composition of claim 1, wherein the composition further comprises a chelator.

9. The deodorant composition of claim 1, wherein the composition is free of baking soda.

10. The deodorant composition of claim 2, further comprising a secondary antimicrobial chosen from hexamidine, magnesium carbonate, zinc carbonate, thymol, sodium carbonate, magnesium carbonate hydroxide, calcium carbonate, polyvinyl formate, salycilic acid, niacinamide, cinnamon essential oil, cinnamon bark essential oil, cinnamic aldehyde, piroctone olamine, polydiallyldimethylammonium chloride, polyquaternium, or mixtures thereof.

11. A deodorant composition comprising:
   a. from about 5% to about 20%, by weight of the composition, of partially carbonated magnesium hydroxide;
   b. from about 10% to about 30% water, by weight of the composition;
   c. from about 30% to about 55%, by weight of the composition, of dipropylene glycol;
   d. a perfume; and
   e. a buffering agent comprising sodium hydroxide;
   wherein the deodorant composition is substantially free of aluminum.

12. The deodorant composition of claim 11, wherein the composition has a pH of at least about 10.

13. The deodorant composition of claim 1, further comprising poloxamine 1307.

14. The deodorant composition according to claim 1, wherein the partially carbonated magnesium hydroxide comprises from about 80% to about 100%, by weight of the partially carbonated magnesium hydroxide, magnesium hydroxide.

15. The deodorant composition of claim 1, wherein the particle size of the magnesium salt is from about 1 micron to about 10 microns.

16. The deodorant composition according to claim 1, wherein the deodorant composition comprises a physically stable structure.

17. The deodorant composition according to claim 11, wherein the partially carbonated magnesium hydroxide comprises from about 80% to about 100%, by weight of the partially carbonated magnesium hydroxide, magnesium hydroxide.

18. The deodorant composition according to claim 11, wherein the partially carbonated magnesium hydroxide comprises magnesium carbonate and from about 80% to about 98%, by weight of the partially carbonated magnesium hydroxide, magnesium hydroxide.

19. The deodorant composition according to claim 11, wherein the deodorant composition comprises a physically stable structure.

* * * * *